United States Patent [19]
Fareed

[11] Patent Number: 5,441,058
[45] Date of Patent: Aug. 15, 1995

[54] METHOD FOR TREATING CARPAL TUNNEL SYNDROME

[76] Inventor: Donald O. Fareed, 801 Buena Vista Ave., Santa Barbara, Calif. 93108

[21] Appl. No.: 137,629

[22] Filed: Oct. 15, 1993

[51] Int. Cl.⁶ ............................................. A61F 5/04
[52] U.S. Cl. ................................ 128/898; 128/878; 128/881; 602/20
[58] Field of Search ................ 602/20, 21, 22; 128/878, 898, 774, 877, 879, 881, 744; 606/201

[56] References Cited

U.S. PATENT DOCUMENTS

| | | | |
|---|---|---|---|
| 3,439,673 | 4/1969 | Sprecher | 128/877 |
| 4,883,073 | 11/1989 | Aziz | 602/21 |
| 4,899,763 | 2/1990 | Sebastian | 128/879 |
| 4,966,137 | 10/1990 | Davini | 602/21 |
| 5,152,302 | 10/1992 | Fareed | 128/878 |
| 5,295,951 | 3/1994 | Fareed | 128/878 |

OTHER PUBLICATIONS

Hammacher Schlemmer 1993 Catalog p. 55 "Elbow Shock Absorber".

Primary Examiner—Michael A. Brown
Assistant Examiner—David J. Kenealy
Attorney, Agent, or Firm—Michael G. Petit

[57] ABSTRACT

An adjustable strap or band adapted to be circumferentially fitted around the forearm to alleviate the symptoms of carpal tunnel syndrome (CTS). The strap is a generally band-shaped device having two opposing inwardly protruding structures on its forearm contacting surface to direct bipolar (transaxial) compression against the radial extensor, supinator complex and flexor muscles when the band is circumferentially tensioned and fastened in place around the forearm. In its preferred form, the band applies an adjustable pressure principally upon the extensor, supinator and flexor muscle wads permitting unimpeded blood circulation along all other portions of the forearm. The two opposing structures that apply transaxial compression are limited in their circumferential extent to those areas of the band immediately overlying the extensor and flexor muscle mass.

1 Claim, 3 Drawing Sheets

METHOD FOR TREATING CARPAL TUNNEL SYNDROME

BACKGROUND OF THE INVENTION

1. Field of the Invention

The present invention relates generally to an adjustable compression arm band and, more specifically, to an arm band constructed to be worn by persons suffering from symptoms of carpal tunnel syndrome.

2. Reference to Patent Application

Reference is made to patent application Ser. No. 07/976,646 filed Nov. 13, 1992 now U.S. Pat. No. 5,295,951 entitled: Device and Method for Treating Tennis Elbow by the present inventor.

3. Prior Art

Carpal tunnel syndrome is the most common entrapment neuropathy of the upper extremity. Because of increased awareness on the part of physicians and the public, the syndrome is now recognized and managed by primary care physicians and occupational health workers as well as hand surgeons. The term "syndrome" means a combination of signs and/or symptoms that form a distinct clinical picture indicative of a particular disorder. Thus, the term "carpal tunnel syndrome" as used herein refers to a particular complex of symptoms and not to a particular etiology. The carpal tunnel represents a canal having affixed space with a finite volume. Any increase in the volume of the contents of the carpal tunnel will correspondingly raise the pressure within the canal. A number of conditions such as obesity or pregnancy can increase the contents or decrease the size of the carpal tunnel and thereby compress the median nerve. Anomalous muscles and osseous and foreign bodies in the carpal tunnel may also compress the median nerve. Similarly, any condition that produces edema in the hand and wrist may cause or accentuate carpal tunnel compression. A non-specific thickening of the tenosynovium appears to be the most common cause of carpal tunnel syndrome. This condition is characterized by thickening of the tenosynovium, which increases the volume of the structures within the carpal tunnel. Tenosynovitus is usually considered nonspecific but may be associated with gout or rheumatoid arthritis or, in fact, many other conditions.

Clinically, a careful physical examination with objective testing are important steps in evaluating the compressive nerve lesions The median nerve innervates the thumb, index and long fingers and the radial side of the ring finger. The symptoms of carpal tunnel syndrome may occur in any of these fingers, although most frequently hyperestheia, paraesthesia or hypoesthesia is observed in the middle (long) finger. Such symptoms are indicative of compression of the median nerve although not necessarily in the carpal tunnel. The wrist flexion test, or Phalen's test, is positive in more than 60% of patients and is considered strong evidence for carpal tunnel syndrome. The test is accomplished by having the patient hold the wrist in a maximally flexed posture. This increases the pressure on the median nerve and reproduces the symptoms of paraesthesia in the digits of the median nerve distribution.

While the severity of symptoms will normally determine the method of treating carpal tunnel syndrome, the treatment can be roughly divided into surgical and non-surgical. If the pain is not great or if the symptoms are of very brief duration, non surgical intervention is usually attempted. Such non-surgical intervention may include splinting to immobilize the wrist and/or the injection of an anti-inflammatory such a cortisone into the tendons passing through the carpal tunnel to reduce the inflammation. Such splinting restricts the use of the affected hand and care must be taken to inject directly into the median nerve. It would be desirable to provide a non surgical method of treating the symptoms of carpal tunnel syndrome which does not require the immobilization of the wrist or injection of steroid. Surprisingly, the present invention has found that a transaxial compression band when applied to the forearm is useful for treating the symptoms of carpal tunnel syndrome with only minimal impairment of the normal circulation up and down the arm.

SUMMARY OF THE INVENTION

It is noted that the above referenced tests elucidate a particular symptomology but provide no information regarding the etiology of "carpal tunnel syndrome". Repetitive motion activities frequently are associated with repetitive or protracted wrist extension, repetitive or protracted forearm pronation or a combination thereof. None of these activities normally would be expected to compress or otherwise compromise the carpal tunnel, yet they create these complaints. In the workplace, the complaint frequently has bilateral occurrence. Splinting the wrist seldom resolves the symptoms associated with carpal tunnel syndrome. The present inventor has observed that local injection of the radial supinator canal usually gives far greater and more pronounced relief of the condition than injection of the wrist. This suggests that the compression of the median nerve may be occurring in the forearm rather than in the carpal tunnel.

The invention provides an adjustable band to be worn by a patient presenting the symptoms of carpal tunnel syndrome. The invention comprises a band means for applying transaxial pressure selectively to the extensor, flexor and supinator muscles (target tissues) of the forearm while, at the same time, not substantially compressing non-target tissues of the forearm. Prior art circular armbands merely function as a tourniquet to impede blood flow up the arm. It is, therefore, an object of this invention to provide a compression band for use on the forearm which will apply transaxial compression selectively to the flexor, extensor and supinator muscle masses in the forearm without substantially compressing non-target tissues.

It is still another object of this invention to provide a compression band for use around the forearm comprising a substantially inelastic strap with two discrete, inwardly protruding skin-contacting members on the forearm-facing surface of the strap for selectively pressing against the flexor and extensor muscles.

Another object of this invention is to provide a forearm compression band with means on the inner surface thereof for selectively applying transaxial countercompression against the extensor and flexor muscle wad where said countercompression means may be easily adjusted by the user while in use.

These and other objects of the invention will soon become apparent as we turn now to the drawings.

DESCRIPTION OF THE PREFERRED EMBODIMENT

Figure 1:
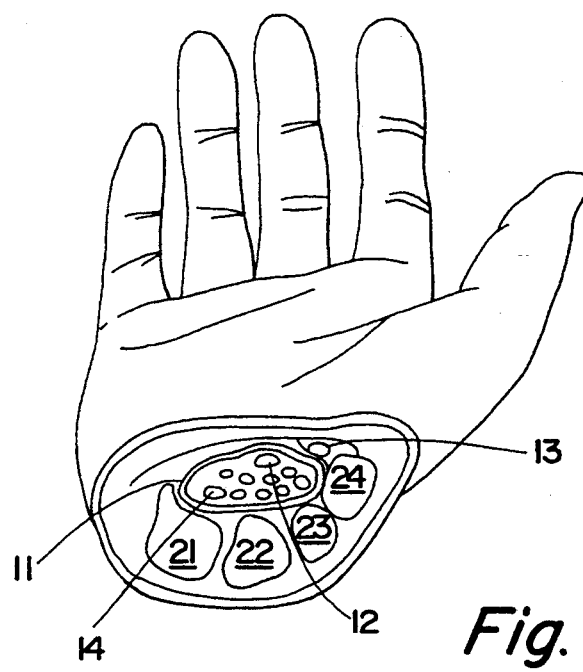
FIG. 1 is a perspective view of a hand cutaway at the wrist showing the carpal tunnel and related structures.

A cross section of the carpal tunnel is shown in FIG. 1. The carpal bones comprising the hamate, 21, capitate 22, trapezoid 23 and trapezium 24, which are tightly bound together, form the dorsal, medial and lateral walls of the tunnel. These bones are joined anteriorly by the transverse carpal ligament 25, a dense, non resilient structure. The carpal tunnel 11 contains the median nerve as well as 9 flexor tendons 14 and their flexor sheaths.

Figure 2:
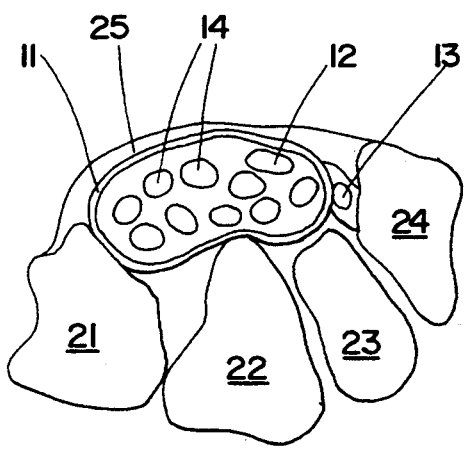
FIG. 2 shows a cross-sectional view of a normal carpal tunnel.
Figure 3:
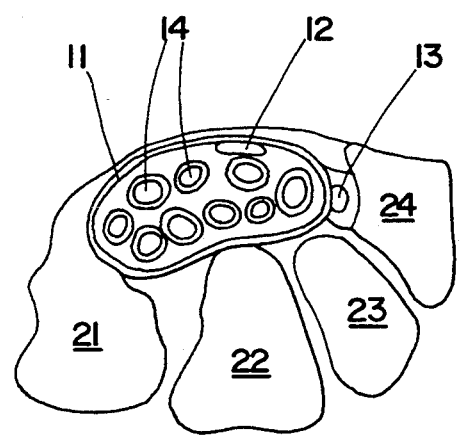
FIG. 3 show a cross-sectional view of a carpal tunnel with tendon sheath thickening.

In FIG. 2, the median nerve 12 and flexor tendons 14 lie within the carpal tunnel 11. Any condition which alters the space within the carpal tunnel 11 may result in median nerve 12 compression. For example, turning now to FIG. 3, thickening of the tendon sheaths 14 within the carpal tunnel will decrease the space available within the tunnel and thereby compress the median nerve. Conversely, any device which would reduce the cross section or volume of objects such as tendons which pass through the carpal tunnel would decrease the pressure on the median nerve and relieve symptoms associated with carpal tunnel syndrome. Surprisingly, it has been found that the simultaneous application of pressure to the flexor and extensor muscle wads in the forearm have the effect of relieving the symptoms of carpal tunnel syndrome. While the mechanism whereby transaxial compression reduces the pressure on the median nerve is not well understood at this time, several possible therapeutic modalities suggest themselves. One might be by preventing bone encroachment on the carpal tunnel by the bones surrounding it such as the capitate, hamate or trapezoid. Another possible mechanism might be that applying pressure on the muscle wad lengthens the muscle and decreases the pressure on the tendons thereby reducing inflammation and reducing swelling of the tendon sheath. Yet another view is that the symptoms of carpal tunnel syndrome are caused by pressure on the median nerve, at some point proximal to the wrist and the presented symptoms are referred to the carpal tunnel from, for example, the forearm.

Figure 4:
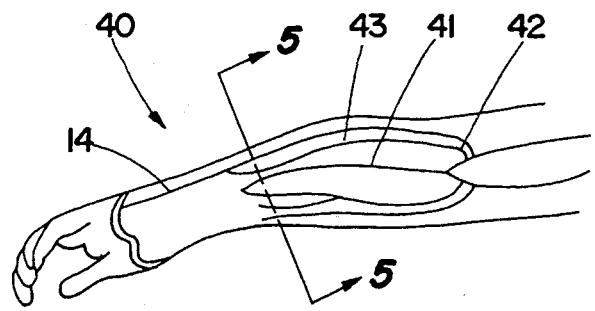
FIG. 4 is a longitudinal cutaway section of a forearm showing the extensor and flexor muscles and tendon.
Figure 5:
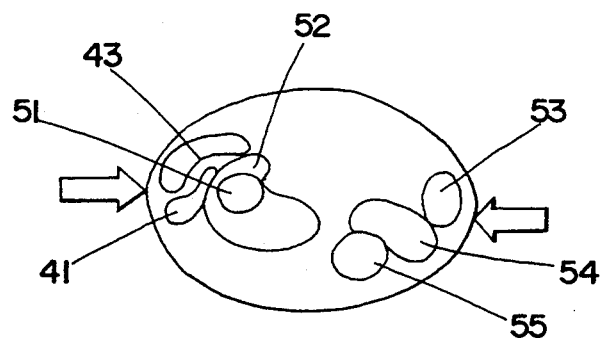
FIG. 5 is a transverse cross-sectional view of the forearm along line 5—5 of FIG. 4 showing the extensor, flexor and supinator muscle wads.

FIG. 4 is a cutaway view of the forearm generally indicated at 40 showing the extensor carpi radialis brevis muscle wad 41 and the extensor carpi radialis brevis muscle wad 43. The lateral epicondyle is indicated at the numeral 42. The extensor radialis muscle groups 41 and 43 "or wads" are elongate more or less sausage shaped muscles enclosed in a fascia. The cross-section of the sausage-shaped flexor and extensor muscles is shown in FIG. 5. The radial supinator complex 52 surrounds the radius 51 and directly underlies the extensor muscles 41 and 43. As used herein, the term "transaxial compression" or alternatively, "transaxial countercompression," refers to opposing pressure applied across the forearm in the general direction of the two broad arrows. Transaxial compression is similar to placing a forefinger over the extensor muscle of the forearm and a thumb over the flexor muscle and pinching. It is seen that such transaxial countercompression will simultaneously compress the extensor muscles 41, 43 and the underlying supinator muscle 52 and the opposing flexor muscles 53 and 54 adjacent to the ulna 55.

The median nerve, in addition to traversing the carpal tunnel, also traverses the intermuscular plane between the supinator 52 and extensor muscles 41 and 43. Contraction and relaxation of these muscles does not pump blood from the muscles because the elastic skin surrounding the muscles expands and relaxes as the muscles contract and relax. A transaxial forearm compression band forms an inelastic outer "wall" around these muscles. Since in the confines of an armband the intermittent relaxation and expansion of these underlying muscles cannot cause distension of the overlying skin, the blood is pumped from the tissue underlying the band compression points thereby reducing the volume of the tissue and the concomitant pressure on the median nerve in the intermuscular plane.

Figure 6A:
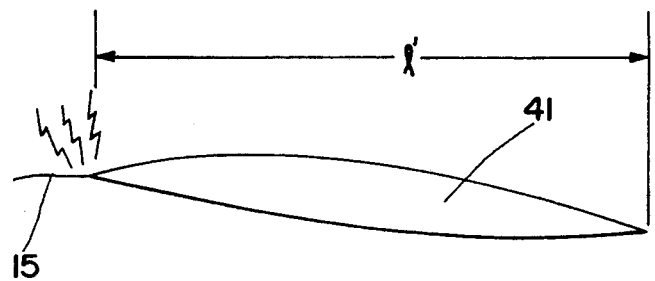
FIG. 6A is a schematic view of an inflamed muscle and tendon in a rest position.
Figure 6B:
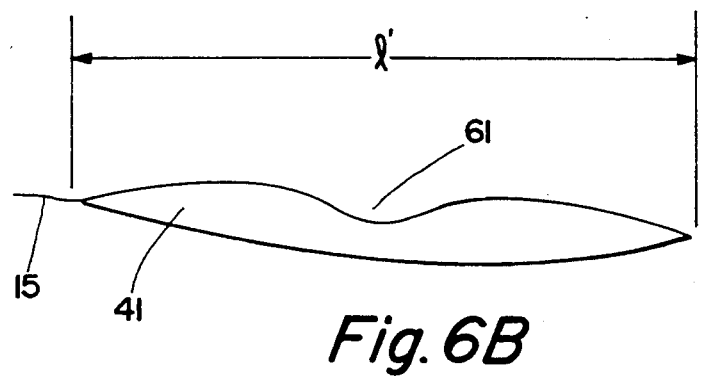
FIG. 6B is a schematic view of the muscle of 6A showing the increase in muscle length a resulting from an applied pressure.

Turning now to FIGS. 6A and B, still another possible mechanism for symptomatic relief of median nerve compression is suggested. In FIGS. 6A and 6B an inflamed arbitrary muscle, for example, the extensor carpi radialis brevis "wad" is shown. FIG. 6A depicts the wad under tension. The tenderness in connecting tendons 15 is aggravated by tension on the wad such as occurs during movement of the wrist. In such a case, the length of the wad is shortened causing stretching of the tendon. In FIG. 6B, the wad is compressed at a point 61 along its length. Since the wad is enclosed in a fascia and is substantially non compressible, the compression causes the muscle wads resting length l to increase to a new length l' where l' is greater than l. Lengthening the muscle wad generates slack therein and relieves the tension on the connecting tendon 15 with concomitant relief of the associated pain.

It is noted that the forearm is substantially elliptical in cross section. A circular band applied to the forearm for the purpose of applying pressure to the wad will preferentially apply pressure at the greatest diameter of the ellipse thereby compressing the underlying blood vessels and impeding blood circulation. It is, therefore, desirable to provide the encircling portion of the compression band with an asymmetry such that only the flexor, supinator and extensor muscles are substantially compressed by the band.

Figure 7:
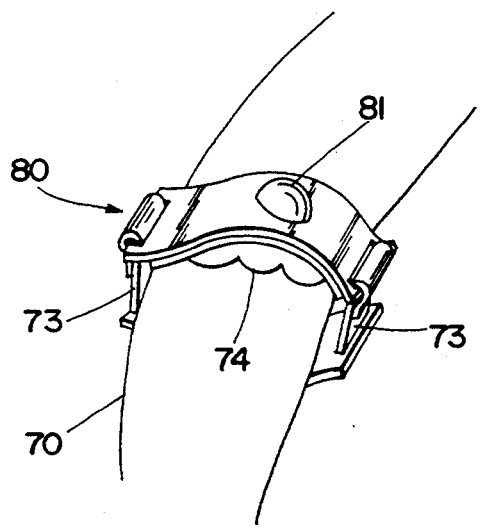
FIG. 7 is a view of the transaxial compression arm band showing the arm band circumferentially positioned about an arm.
Figure 8:
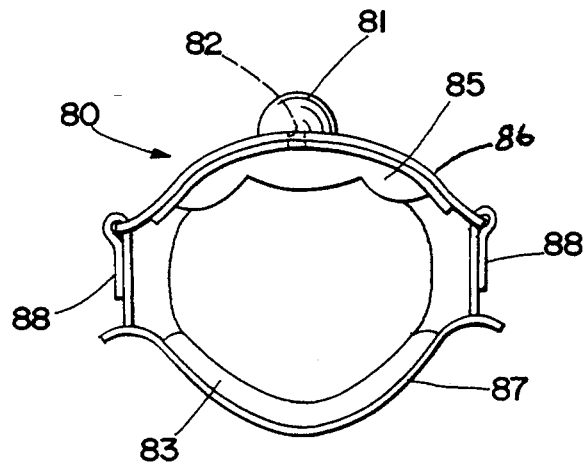
FIG. 8 is a front view of the arm band of FIG. 7.
Figure 9:
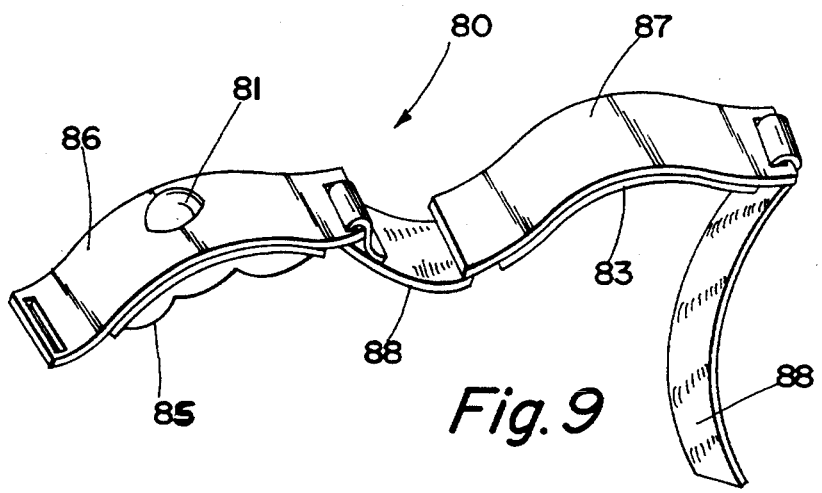
FIG. 9 is a perspective view of the transaxial compression band of the present invention.

Such an asymmetry is shown generally in FIG. 7 and in more detail in one preferred embodiment shown in FIG. 8. In FIG. 7, a band 80 is shown encircling the forearm 70. The band 80 has inner skin contacting surfaces 71 with discontinuities or gaps between the band 80 and the skin at 73. The positions of the discontinuities 73 are such that they overly the non-target tissues to minimize pressure thereon. When in use, the encircling band may be positioned about the forearm to align the discontinuities 73 to overlie the non-target tissues of the forearm. The two opposing protuberances 74 (only one is shown in FIG. 7) may then be positioned to overlie the extensor and flexor wad and the band tightened. The presence of the discontinuities about the inner circumference of the band which space the band from the arm will enable unrestricted circulation of the blood while enabling the simultaneous transaxial compression of anatomically opposed muscle groups.

Another preferred embodiment of a compression band according to the teachings of the invention is shown in FIG. 8. The band, generally indicated at 80, has a skin contacting pad 83 and at least one inflatable balloon-like skin-contacting member 85 disposed on its inner surface. A pump 81, which preferably may be operated by finger pressure, is mounted on the outer surface of the band. The pump 81 is in fluid communication with the interior of the inflatable member by means of a channel 82 permitting adjustment to provide the desired pressure against the underlying muscle group.

The construction of the band 80 is specially adopted to provide transaxial countercompression. The band 80 comprises two substantially "U" shaped inelastic plates: an upper plate 86 and a lower plate 87 linked to one another by one or more adjustable straps 88. In the above embodiment, the inner skin contacting surface of the upper plate 86 comprises one or more inflatable elastomer balloons 85, the pressure within the interior chamber of the balloons being adjustable by means of a finger-activated pump/exhaust 81. The skin contacting surface of the lower plate 87 is conveniently lined with a closed cell foam 83 for comfort. When the strap 80 is securely fastened around the forearm with the opposing skin-contacting surfaces 83 and 85 overlying the extensor and flexor muscles, inflation of the balloon(s) 85 by means of the pump 81 draws the lower plate 87 toward the upper plate 86 thereby providing transaxial countercompression of the flexor, supinator and extensor muscles. While the inflatable member provides a simple means for adjusting the transaxial compression any suitable adjustment means will serve the same purpose.

Figure 10:
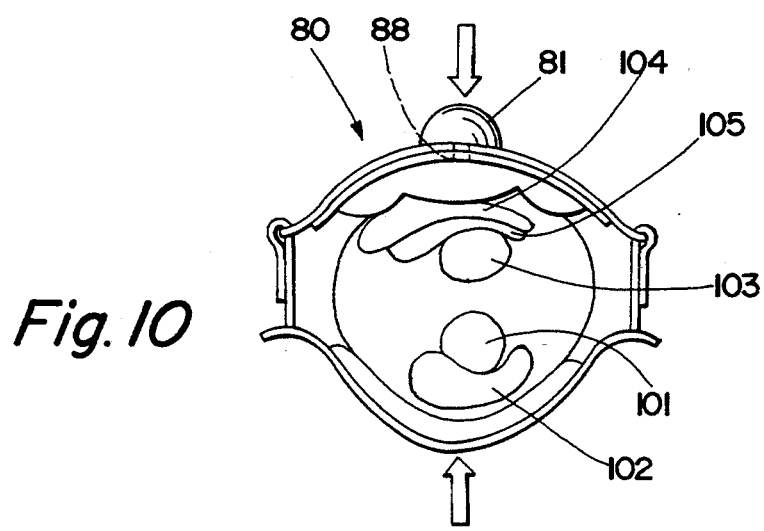
FIG. 10 is a cross-sectional view of the transaxial compression band around the forearm.

The transaxial compression is seen more clearly in FIG. 10. The flexor muscle mass 102 is located adjacent to the ulna 101. The extensor muscle mass 104 lies adjacent to the supinator complex 105 which, in turn, lies adjacent to the radius 103. It is clear that counter compression of the upper and lower plates in the direction of the heavy arrows will compress the flexor, extensor and supinator muscles.

The transaxial compression band of the present invention is useful for treating the symptoms of carpal tunnel syndrome. The band relieves the symptoms while having little adverse effect on circulation. Any devices which rely merely on tightening a circumferential strap around the forearm in order to apply significant compression to the muscle causes the veins to distend and impedes circulation. The transaxial compression band minimizes the tourniquet effect.

It is to be understood that numerous modifications may be made in the illustrated preferred embodiment and other arrangements may be devised without departing from the spirit and scope of the invention as set forth in the appended claims. For example, the inflatable member is one means for adjusting the transaxial compression. This may also be accomplished by merely tightening the band around the forearm or by using thumb screws or the like for adjusting countercompression during use. While particular embodiments of the present invention have been illustrated and described it would be obvious to those skilled in the art that various other changes and modifications can be made without departing from the spirit and scope of the invention. It is therefore intended to cover in the appended claims all such changes and modifications that are within the scope of this invention.

What I claim is:

1. A method for treating the symptoms of carpal tunnel syndrome comprising the following steps:
    (a) presenting a generally circular device having two discrete compression plates projecting inwardly from the circular device and located at anatomically opposed positions along the circumference of the device;
    (b) placing the device around the forearm to encircle at least a portion of the forearm so that said discrete compression plates overly respectively the flexor and extensor muscles in the forearm at a portion on the forearm that is closer to the elbow than the wrist; and
    (c) drawing said compression plates toward one another to apply bipolar transaxial compression of equal magnitude simultaneously to discrete areas of the skin directly overlying the flexor and the extensor muscles of the proximal portion of the forearm without substantial compression of other skin on the forearm.

* * * * *